United States Patent
Rohrer et al.

(10) Patent No.: US 11,727,571 B2
(45) Date of Patent: Aug. 15, 2023

(54) FORECAST OF MRI IMAGES BY MEANS OF A FORECAST MODEL TRAINED BY SUPERVISED LEARNING

(71) Applicant: BAYER AKTIENGESELLSCHAFT, Leverkusen (DE)

(72) Inventors: Martin Rohrer, Berlin (DE); Arthur Uber, III, Pittsburgh, PA (US)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 17/753,838

(22) PCT Filed: Sep. 14, 2020

(86) PCT No.: PCT/EP2020/075593
§ 371 (c)(1),
(2) Date: Mar. 16, 2022

(87) PCT Pub. No.: WO2021/052896
PCT Pub. Date: Mar. 25, 2021

(65) Prior Publication Data
US 2022/0343505 A1 Oct. 27, 2022

(30) Foreign Application Priority Data
Sep. 18, 2019 (EP) ..................... 19197989

(51) Int. Cl.
*G06K 9/00* (2022.01)
*G06T 7/00* (2017.01)
(Continued)

(52) U.S. Cl.
CPC ............ *G06T 7/0016* (2013.01); *A61B 5/004* (2013.01); *A61B 5/055* (2013.01);
(Continued)

(58) Field of Classification Search
CPC ....... A61B 5/055; A61B 5/0263; A61B 6/481; A61B 8/481; A61B 34/10–2034/101;
(Continued)

(56) References Cited

U.S. PATENT DOCUMENTS

| 732,697 A | 7/1903 | Bates |
|---|---|---|
| 5,732,697 A | 3/1998 | Zhang et al. |

(Continued)

FOREIGN PATENT DOCUMENTS

| CN | 104769641 A | 7/2015 |
|---|---|---|
| CN | 107492090 A | 12/2017 |

(Continued)

OTHER PUBLICATIONS

Coulden; Richard, "State-of-the-Art Imaging Techniques in Chronic Thromboembolic Pulmonary Hypertension", Proceedings of the American Thoracic Society, 2006, vol. 3, 577-583.
(Continued)

*Primary Examiner* — Atiba O Fitzpatrick
(74) *Attorney, Agent, or Firm* — Stephan Voelkening; David Schramm (57) ABSTRACT

The present disclosure deals with the quickening of MRI examinations. Subjects of the present disclosure are a method, a system, a computer program product, a use, a contrast agent for use and a kit.

19 Claims, 4 Drawing Sheets

(51) Int. Cl.
*A61B 5/00* (2006.01)
*A61B 5/055* (2006.01)

(52) U.S. Cl.
CPC .............. *G06T 2207/10088* (2013.01); *G06T 2207/20084* (2013.01); *G06T 2207/30056* (2013.01); *G06T 2207/30101* (2013.01)

(58) Field of Classification Search
CPC ............. G06T 2207/10088–10096; G06T 2207/20081; G06T 2207/20084; G06T 11/00; G06T 2200/00–08; G06T 2210/00; G06T 2210/41; G06T 2211/00; G06T 7/0016; G06T 2207/30056; G06T 2207/30101; G06T 2207/30104; G01R 33/5608; G01R 33/5635; G01R 33/5601; A61K 49/06; G06V 10/454; G06V 10/82; G06V 10/70; G06V 10/774–7796; G06V 10/778–7792; G06V 2201/031; G06K 9/6256; G06K 9/6257; G06K 9/6259; G06K 9/6263; G06N 3/02–126; G06N 20/00–20; G06N 3/084; G16H 50/50

See application file for complete search history.

(56) References Cited

U.S. PATENT DOCUMENTS

| | | |
|---|---|---|
| 5,840,026 A | 11/1998 | Uber, III et al. |
| 6,039,931 A | 3/2000 | Schmitt-Willich et al. |
| 6,643,537 B1 | 11/2003 | Zatezalo et al. |
| 6,754,376 B1 | 6/2004 | Turek et al. |
| 6,819,790 B2 | 11/2004 | Suzuki et al. |
| 7,564,990 B2 | 7/2009 | Kern et al. |
| 7,738,683 B2 | 6/2010 | Cahill et al. |
| 7,937,134 B2 | 5/2011 | Uber et al. |
| 7,949,167 B2 | 5/2011 | Krishnan et al. |
| 3,060,178 A1 | 11/2011 | Zhou et al. |
| 8,155,406 B2 | 4/2012 | Mattiuzzi |
| 9,311,702 B2 | 4/2016 | Pautot |
| 9,449,381 B2 | 9/2016 | Liang |
| 9,616,166 B2 | 4/2017 | Kalafut et al. |
| 9,754,371 B2 | 9/2017 | Kateb et al. |
| 9,959,615 B2 | 5/2018 | Liang et al. |
| 10,157,467 B2 | 12/2018 | Dincer et al. |
| 10,176,408 B2 | 1/2019 | Paik et al. |
| 10,335,106 B2 | 7/2019 | Kim |
| 10,555,773 B2 | 2/2020 | Higaki et al. |
| 10,645,359 B2 | 5/2020 | Bist et al. |
| 10,933,186 B2 | 3/2021 | Uber, III |
| 11,246,558 B2 | 2/2022 | Uber, III et al. |
| 11,308,613 B2 | 4/2022 | Chitiboi et al. |
| 2005/0100208 A1 | 5/2005 | Suzuki et al. |
| 2006/0018524 A1 | 1/2006 | Suzuki et al. |
| 2007/0047787 A1 | 3/2007 | Oakley et al. |
| 2008/0317315 A1 | 12/2008 | Stemmer |
| 2010/0198054 A1 | 8/2010 | Ewing et al. |
| 2011/0029248 A1 | 2/2011 | Saeed et al. |
| 2013/0035921 A1 | 2/2013 | Rodriguez-Ponce et al. |
| 2013/0297554 A1 | 11/2013 | Mah |
| 2014/0062481 A1 | 3/2014 | Greiser et al. |
| 2014/0257854 A1 | 9/2014 | Becker et al. |
| 2015/0125398 A1 | 5/2015 | Assouline et al. |
| 2016/0000945 A1 | 1/2016 | Nedergaard et al. |
| 2016/0035093 A1 | 2/2016 | Kateb et al. |
| 2016/0038092 A1 | 2/2016 | Golay |
| 2016/0109539 A1 | 4/2016 | Mardor et al. |
| 2017/0243349 A1 | 8/2017 | Hou et al. |
| 2017/0245817 A1 | 8/2017 | Berlin et al. |
| 2017/0269182 A1 | 9/2017 | Beck |
| 2017/0281278 A1* | 10/2017 | Higaki .................. A61B 6/504 |
| 2018/0242917 A1 | 8/2018 | Bagherzadeh et al. |
| 2018/0315183 A1 | 11/2018 | Milioni De Carvalho et al. |
| 2019/0012932 A1 | 1/2019 | Higaki et al. |
| 2019/0099145 A1 | 4/2019 | Kim |
| 2019/0122348 A1* | 4/2019 | Jensen .................. G06T 11/00 |
| 2019/0310338 A1 | 10/2019 | James et al. |
| 2019/0317171 A1 | 10/2019 | Nayak et al. |
| 2019/0318474 A1* | 10/2019 | Han .................. G06V 10/764 |
| 2019/0362522 A1* | 11/2019 | Han .................. A61B 5/0035 |
| 2019/0365340 A1 | 12/2019 | Hao et al. |
| 2020/0167911 A1 | 5/2020 | Park et al. |
| 2020/0202557 A1 | 6/2020 | Schmidt |
| 2020/0242744 A1* | 7/2020 | Schafer ................ G06T 15/08 |
| 2020/0258629 A1 | 8/2020 | Ahmad et al. |
| 2020/0311932 A1* | 10/2020 | Hooper .................. G06N 3/088 |
| 2020/0371182 A1 | 11/2020 | Grimm et al. |
| 2021/0012486 A1* | 1/2021 | Huang .................. G06N 3/08 |
| 2021/0027436 A1* | 1/2021 | Banerjee ................ G06T 5/009 |
| 2021/0027502 A1 | 1/2021 | Abumoussa et al. |
| 2021/0056734 A1* | 2/2021 | Han .................... A61B 5/055 |
| 2021/0386389 A1* | 12/2021 | Freiman .................. G06N 3/08 |
| 2022/0018924 A1 | 1/2022 | Bai et al. |
| 2022/0031270 A1 | 2/2022 | Cohen et al. |
| 2022/0105265 A1 | 4/2022 | Cowan et al. |
| 2022/0351369 A1 | 11/2022 | Haase et al. |

FOREIGN PATENT DOCUMENTS

| | | |
|---|---|---|
| CN | 109983474 A | 7/2019 |
| EP | 1941460 A1 | 7/2008 |
| EP | 2626718 A1 | 8/2013 |
| EP | 2750102 A1 | 7/2014 |
| EP | 3118644 A1 | 1/2017 |
| EP | 3322997 A1 | 5/2018 |
| EP | 3619631 A1 | 3/2020 |
| EP | 3804615 A1 | 4/2021 |
| EP | 3875979 A1 | 9/2021 |
| JP | 5878009 B2 | 3/2016 |
| KR | 102001398 B1 | 7/2019 |
| WO | 2007053676 A2 | 5/2007 |
| WO | 2009135923 A1 | 11/2009 |
| WO | 2012075577 A1 | 6/2012 |
| WO | 2013121374 A2 | 8/2013 |
| WO | 2014162273 A1 | 10/2014 |
| WO | 2016007734 A1 | 1/2016 |
| WO | 2017040152 A1 | 3/2017 |
| WO | 2017139110 A1 | 8/2017 |
| WO | 2018046412 A1 | 3/2018 |
| WO | 2018183044 A1 | 10/2018 |
| WO | 2018200493 A1 | 11/2018 |
| WO | 2018202541 A1 | 11/2018 |
| WO | 2019046299 A1 | 3/2019 |
| WO | 2019063520 A1 | 4/2019 |
| WO | 2019074938 A1 | 4/2019 |
| WO | 2019102846 A1 | 5/2019 |
| WO | 2019204406 A1 | 10/2019 |
| WO | 2019241659 A1 | 12/2019 |
| WO | 2021052850 A1 | 3/2021 |
| WO | 2021069338 A1 | 4/2021 |
| WO | 2021069343 A1 | 4/2021 |
| WO | 2021197996 A1 | 10/2021 |

OTHER PUBLICATIONS

Delcroix Marion; et al, "Chronic Thromboembolic Pulmonary Hypertension; Epidemiology and Risk Factors", Annals of the American Thoracic Society, Jul. 2016, vol. 13 Supp. 13, S201-S206.

"FDA Reclassification Letter regarding OsteoDetect", May 24, 2018.

Galie Nazzareno; et al, "2015 ESC/ERS Guidelines for the diagnosis and treatment of pulmonary hypertension", European Heart Journal, Jan. 2016, vol. 37, Issue 1, 67-119.

Hachulla; et al, "Dual-energy computed tomographic imaging of pulmonary hypertension", Swiss Medical Weekly, 2016, 146; w14328, 1-20.

"International Preliminary Report on Patentability from PCT Application No. PCT/US2020/021861", dated Sep. 23, 2021.

Smith; Dana, "Artificial Intelligence Can Detect Alzheimer's Disease in Braine Scans Six Years Before a Diagnosis", Jan. 2, 2019.

Tapson Victor; et al, "Incidence and Prevalence of Chronic

(56) References Cited

OTHER PUBLICATIONS

Thromboembolic Pulmonary Hypertension", Proceedings of the American Thoracic Society, Sep. 7, 2006, vol. 3, 564-567.

Wang; et al, "Stacked Fully Convolutional Networks for Pulmonary Vessel Segmentation", IEEE Visual Communications and Image Processing (VCIP), 2018.

Bellani; Giacomo et al, "Epidemiology, Patterns of Care, and Mortality for Patients With Acute Respiratory Distress Syndrome in Intensive Care Unites in 50 Countries", JAMA, 2016.

Choi; Jun-Ho et al, "EmbraceNet: A robust deep learning architecture for multimodal classification", Information Fusion, 2019, 51, 259-270.

Gong Enhao; et al, "Deep Learning Enables Reduced Gadolinium Dose for Contrast-Enhanced Brain MRI", J. Magn. Reson. Imaging, 2018, 48, 330-340.

"Information on Primovist", 2016.

"International Preliminary Report on Patentability from PCT Application No. PCT/EP2020/077767", Apr. 12, 2022.

"Introduction to Multimodal Learning Model", DEV Community, Feb. 5, 2019.

Rajpurkar; Pranav et al, "CheXNet: Radiologist-Level Pneumonia Detection on Chest X-Rays with Deep Learning", 2017.

Yasaka Koichiro; et al, "Deep Learning with Convolutional Neural Network for Differentiation of Liver Masses at Dynamic Contrast-enhanced CT: A Preliminary Study", Radiology, Mar. 2018, vol. 286; No. 3, 887-896.

Baccouche; et al, "Sequential Deep Learning for Human Action Recognition", International Workshop on Human Behavior Understanding, 2011, 29-39.

Caraiani; et al, "Description of Focal Liver Lesions With GD-EOB-DTPA Enhanced MRI", Clujul Medical, 2015, vol. 88 No. 4, 438-448.

Chiusano; et al, "DCE-MRI Analysis Using Sparse Adaptive Representations", 2011, 67-74.

Frydrychowicz; et al, "Hepatobiliary MR Imaging with Gadolinium Based Contrast Agents", J Magn Reson Imaging, Mar. 2012, 35 (3), 492-511.

Ghodasara; Satyam et al, "Quantifying Perfusion Properties with DCE-MRI Using a Dictionary Matching Approach", International Society for Magnetic Resonance in Medicine, ISMRM,, Jun. 1, 2018.

"International Preliminary Report on Patentability from PCT Application No. PCT/EP2020/075593", Mar. 31, 2022.

"International Preliminary Report on Patentability from PCT Application No. PCT/IB2020/058688", dated Mar. 31, 2022.

"International Search Report and Written Opinion from PCT Application No. PCT/IB2020/058688", dated Dec. 9, 2020.

Ji; et al, "3D Convolutional Neural Networks for Human Action Recognition", IEEE Transactions on Pattern Analysis and Machine Intelligence, Jan. 2013, vol. 35 No. 1, 221-231.

Karpathy; et al, "Large-scale Video Classification with Convolutional Neural Networks", Proceedings of the IEEE Conference on Computer Vision and Pattern Recognition, 2014, 1725-1732.

Khan; et al, "Chapter 3.3 "Neural Networks Basics"", A Guide to Convolutional Neural Networks for Computer Vision, Morgan & Claypool Publishers, 2018, pp. 36-39.

Kim; et al, "Arterial subtraction images of gadoxetate-enhanced MRI improve diagnosis of early-stage hepatocellular carcinoma", Journal of Hepatology, 2019, vol. 71, 534-542.

Kwon; et al, "Differentiation of small (less than or equal to cm) hepatocellular carcinomas from small benign nodules in cirrhotic liver on gadoxetic acid-enhanced and diffusion-weighted magnetic resonance images", Abdominal Imaging, Jul. 6, 2014, pp. 64-78.

Shtern; Alon, "Shape Correspondence Using Spectral Methods and Deep Learning Research Thesis", Aug. 2017.

Simonyan; et al, "Two-Stream Convolutional Networks for Action Recognition in Videos", Advances in Neural Information Processing Systems, 2013, 568-576.

Thompson; et al, "Indicator Transit Time Considered as a Gamma Variate", Circulation Research, Jun. 1964, vol. XIV, 502-515.

Weizman; et al, "Prediction of Brain MR Scans in Longitudinal Tumor Follow-Up Studies", Oct. 1, 2012, pp. 179-187.

Bannas; et al, "Combined Gadoxetic Acid and Gadofosveset Enhanced Liver MRI: A Feasibility and Parameter Optimization Study", Magnetic Resonance in Medicine, 2016, 75, 318-328.

Baytas Inci M.; et al, "Patient Subtyping via Time-Aware LSTM Networks", 2017.

Cannella; et al, "Common pitfalls when using the Liver Imaging Reporting and Data System (LI-RADS): lessons learned from a multi-year experience", Abdominal Imaging, Aug. 2, 2018, 43-53.

Conversano; et al, "Hepatic Vessel Segmentation for 3D Planning of Liver Surgery: Experimental Evaluation of a New Fully Automatic Algorithm", Academic Radiology, Apr. 2011, vol. 18/ No. 4, 461-470.

Fischer; et al, "Ultra-high-field imaging of the biliary tract of 7 Tesla: initial results of Gd-EOB-DTPA-enhanced MRCP", Proc. Intl. Soc. Mag. Reson. Med., 2012, 20.

Hope; et al, "Improvement of Gadoxetate Arterial Phase Capture With a High Spatio-Temporal Resolution Multiphase Three-Dimensional SPGR-Dixon Sequence", Journal of Magnetic Resonance Imaging, 2013, 38, 938-945.

Huang Gao.; et al, "Densely Connected Convolutional Networks", Jan. 28, 2018.

"International Preliminary Report on Patentability from PCT Application No. PCT/EP2020/075288", dated Mar. 31, 2022.

"International Preliminary Report on Patentability from PCT Application No. PCT/EP2020/077775", dated Apr. 12, 2022.

Kim; et al, "Gadoxetic acid-enhanced magnetic resonance imaging: Hepatocellular carcinoma and mimickers", Clinical and Molecular Hepatology, Sep. 2019, vol. 25 No. 3, 223-233.

Knobloch; et al, "Combined Gadoxetic Acid and Gadobenate Dimeglumine Enhanced Liver MRI for Liver Metastasis Detection: A Parameter Optimization Study", Proc. Intl. Soc. Mag. Reson. Med., 2018.

Le; Quoc V., "A Tutorial on Deep Learning Part 2: Autoencoders, Convolutional Neural Networks and Recurrent Neural Networks", Oct. 20, 2015.

Marcan; et al, "Segmentation of hepatic vessels from MRI images for planning of electroporation-based treatments in the liver", Radiol. Oncol., 2014, 48 (3), 267-281.

Meng Qinxue; et al, "Relational Autoencoder for Feature Extraction", Feb. 9, 2018.

Moccia; et al, "Blood vessel segmentation algorithms—Review of methods, datasets and evaluation metrics", Computer Methods and Programs in Biomedicine, 2018, 158, 71-91.

Lusic Hrvoje; et al, "X-Ray Computed Tomography Contrast Agents", Chem. Rev., 2013.

Xiao; Yu-Dong et al, "MRI contrast agents: Classification and application (Review)", International Journal of Molecular Medicine, 2016, 38, 1319-1326.

Chibuzo; Abonyi et al, "Intravascular Contrast Media in Radiography: Historical Development & Review of Risk Factors for Adverse Reactions", South American Journal of Clinical Research, 2016, Vo. 3, Issue 1.

Ignee; Andre et al, "Ultrasound contrast agents", Endoscopic Ultrasound, Nov.-Dec. 2016, vol. 5, Issue 6, 355-362.

Karani Neerav et al: "Temporal Interpolation of Abdominal MRIs Acquired During Free-Breathing", Sep. 4, 2017 (Sep. 4, 2017), 12th European Conference on Computer Vision, ECCV 2012; [Lecture Notes in Computer Science], Springer Berlin Heidelberg, Berlin, Heidelberg, pp. 359-367, XP047528114, ISSN: 0302-9743 ISBN: 978-3-642-39453-9.

Nouh Mohamed; et al, "Radiographic and magnetic resonances contrast agents: Essentials and tips for safe practices", World Journal of Radiology, Sep. 28, 2017, vol. 9, Issue 9, 339-349.

Qin Chen et al: "Convolutional Recurrent Neural Networks for Dynamic MR Image Reconstruction", IEEE Transactions on Medical Imaging, IEEE Service Center, Piscataway, NJ, US, Bd. 38, Nr. 1, Jan. 1, 2019 (Jan. 1, 2019), Seiten 280-290, P011694961, ISSN: 0278-0062, DOI: 10.1109/TMI.2018.2863670.

Smits Loek; et al, "Evaluation of ultrasmall superparamagnetic iron oxide (USPIO) enhanced MRI with ferumoxytol to quantify arterial wall inflammation", Atherosclerosis, 2017, 263, 211-218.

(56) References Cited

OTHER PUBLICATIONS

Takeshima, Hidenori: "Integrating Spatial and Temporal Correlations into a Deep Neural Network for Low-delay Reconstruction of Highly Undersampled Radial Dynamic Images", International Society for Magnetic Resonance in Medicine, ISMRM, 2030 Addison Street, 7th Floor, Berkeley, CA 94704 USA, pp. 2796, Jun. 1, 2018 (Jun. 1, 2018).

"Written Opinion from PCT Application No. PCT/EP2021/057689", dated Jun. 24, 2021.

\* cited by examiner

FORECAST OF MRI IMAGES BY MEANS OF A FORECAST MODEL TRAINED BY SUPERVISED LEARNING

CROSS REFERENCE TO RELATED APPLICATIONS

The present application is a U.S. national phase application under 35 U.S.C. § 371 of PCT International Application No. PCT/EP2020/075593, filed 14 Sep. 2020, and claims priority to EP Application No. 19197989.7, filed 18 Sep. 2019, the disclosures of which are incorporated herein in their entirety.

The present disclosure deals with the quickening of MRI examinations, especially in the detection and differential diagnosis of focal liver lesions by means of dynamic contrast-enhancing magnetic resonance imaging (MRI). Subjects of the present disclosure are a method, a system and a computer program product for predicting MRI images, especially of the liver during the hepatobiliary phase.

Magnetic resonance imaging, MRI for short, is an imaging method which is used especially in medical diagnostics for depicting structure and function of the tissue and organs in the human or animal body.

In MRI, the magnetic moments of protons in an examination object are aligned in a basic magnetic field, with the result that there is a macroscopic magnetization along a longitudinal direction. This is subsequently deflected from the resting position by the incident radiation of high-frequency (HF) pulses (excitation). The return of the excited states into the resting position (relaxation) or the magnetization dynamics is subsequently detected by means of one or more HF receiver coils as relaxation signals.

For spatial encoding, rapidly switched magnetic gradient fields are superimposed on the basic magnetic field. The captured relaxation signals or the detected and spatially resolved MRI data are initially present as raw data in a spatial frequency space, and can be transformed by subsequent Fourier transformation into the real space (image space).

In the case of native MRI, the tissue contrasts are generated by the different relaxation times (T1 and T2) and the proton density.

T1 relaxation describes the transition of the longitudinal magnetization into its equilibrium state, T1 being that time that is required to reach 63.21% of the equilibrium magnetization prior to the resonance excitation. It is also called longitudinal relaxation time or spin-lattice relaxation time.

Analogously, T2 relaxation describes the transition of the transversal magnetization into its equilibrium state.

MRI contrast agents develop their action by altering the relaxation times of the structures which take up contrast agents. A distinction can be made between two groups of substances: paramagnetic and superparamagnetic substances. Both groups of substances have unpaired electrons which induce a magnetic field around the individual atoms or molecules.

Superparamagnetic contrast agents lead to a predominant shortening of T2, whereas paramagnetic contrast agents mainly lead to a shortening of T1. A shortening of the T1 time leads to an increase in the signal intensity in T1-weighted MRI images, and a shortening of the T2 time leads to a decrease in the signal intensity in T2-weighted MRI images.

The action of said contrast agents is indirect, since the contrast agent itself does not give off a signal, but instead only influences the signal intensity of the hydrogen protons in its surroundings.

An example of a superparamagnetic contrast agent are iron oxide nanoparticles (SPIO: superparamagnetic iron oxide).

Examples of paramagnetic contrast agents are gadolinium chelates such as gadopentetate dimeglumine (trade name: Magnevist® and others), gadobenate dimeglumine (trade name: Multihance®), gadoteric acid (Dotarem®, Dotagita®, Cyclolux®), gadodiamide (Omniscan®), gadoteridol (ProHance®) and gadobutrol (Gadovist®).

Extracellular, intracellular and intravascular contrast agents can be distinguished according to their pattern of spreading in the tissue.

Contrast agents based on gadoxetic acid are characterized by specific uptake by liver cells, the hepatocytes, by enrichment in the functional tissue (parenchyma) and by enhancement of the contrasts in healthy liver tissue. The cells of cysts, metastases and most liver-cell carcinomas no longer function like normal liver cells, do not take up the contrast agent or hardly take it up, are not depicted with enhancement, and are identifiable and localizable as a result.

Examples of contrast agents based on gadoxetic acid are described in U.S. Pat. No. 6,039,931A; they are commercially available under the trade names Primovist® or Eovist® for example.

The contrast-enhancing effect of Primovist®/Eovist® is mediated by the stable gadolinium complex Gd-EOB-DTPA (gadolinium ethoxybenzyl diethylenetriamine pentaacetic acid). DTPA forms, with the paramagnetic gadolinium ion, a complex which has an extremely high thermodynamic stability. The ethoxybenzyl radical (EOB) is the mediator of the hepatobiliary uptake of the contrast agent.

Primovist® can be used for the detection of tumours in the liver. Blood supply to the healthy liver tissue is primarily achieved via the portal vein (vena *portae*), whereas the liver artery (arteria *hepatica*) supplies most primary tumours. After intravenous injection of a bolus of contrast agent, it is accordingly possible to observe a time delay between the signal rise of the healthy liver parenchyma and of the tumour.

Besides malignant tumours, what are frequently found in the liver are benign lesions such as cysts, haemangiomas and focal nodular hyperplasia (FNH). A proper planning of therapy requires that these be differentiated from the malignant tumours. Primovist® can be used for the identification of benign and malignant focal liver lesions. By means of T1-weighted MRI, it provides information about the character of said lesions. Differentiation is achieved by making use of the different blood supply to liver and tumour and of the temporal profile of contrast enhancement.

The contrast enhancement achieved by means of Primovist® can be divided into at least two phases: into a dynamic phase (comprising the so-called arterial phase, portal-vein phase and late phase) and the hepatobiliary phase, in which a significant uptake of Primovist® into the hepatocytes has already taken place.

In the case of the contrast enhancement achieved by Primovist® during the distribution phase, what are observed are typical perfusion patterns which provide information for the characterization of the lesions. Depicting the vascularization helps to characterize the lesion types and to determine the spatial relationship between tumour and blood vessels.

In the case of T1-weighted MRI images, Primovist® leads, 10-20 minutes after the injection (in the hepatobiliary phase), to a distinct signal enhancement in the healthy liver parenchyma, whereas lesions containing no hepatocytes or only a few hepatocytes, for example metastases or moderately to poorly differentiated hepatocellular carcinomas (HCCs), appear as darker regions.

Tracking the spreading of the contrast agent over time across the dynamic phase and the hepatobiliary phase provides a good possibility of the detection and differential diagnosis of focal liver lesions; however, the examination extends over a comparatively long time span. Over said time span, movements by the patient should be avoided in order to minimize movement artefacts in the MRI image. The lengthy restriction of movement can be unpleasant for a patient.

Proceeding from the described prior art, the technical object was that of making the examination less unpleasant for the patient.

This object is achieved by the subjects of the independent claims. Preferred embodiments of the present disclosure are found in the dependent claims, in this description and in the drawings. By means of the present disclosure, the MRI examination time span is considerably reduced, which makes the experience easier for the patient.

The present disclosure provides, in a first aspect, a computer-implemented method comprising the steps of:
  receiving a plurality of first MRI images, at least some of the first MRI images showing an examination region during a first time span after administering a contrast agent,
  feeding the plurality of first MRI images to a prediction model, the prediction model having been trained on the basis of reference MRI images by means of supervised learning to generate, from first reference MRI images, at least some of which show an examination region during a first time span after administering a contrast agent, one or more second reference MRI images showing the examination region during a second time span, the second time span following the first time span chronologically,
  generating one or more predicted MRI images showing the examination region during a second time span by means of the prediction model, the second time span following the first time span chronologically,
  displaying and/or outputting the one or more predicted MRI images and/or storing the one or more predicted MRI images in a data storage medium.

The present disclosure further provides a system comprising:
a receiving unit,
a control and calculation unit, and
an output unit,
  the control and calculation unit being configured to prompt the receiving unit to receive a plurality of first MRI images, at least some of the first MRI images showing an examination region during a first time span after administering a contrast agent,
  the control and calculation unit being configured to predict one or more second MRI images on the basis of the received first MRI images, the one or more second MRI images showing the examination region during a second time span, the second time span following the first time span chronologically,
  the control and calculation unit being configured to prompt the output unit to display the one or more second MRI images, to output them or to store them in a data storage medium.

The present disclosure further provides a computer program product comprising a computer program which can be loaded into a memory of a computer system, where it prompts the computer system to execute the following steps:
  receiving a plurality of first MRI images, at least some of the first MRI images showing an examination region during a first time span after administering a contrast agent,
  feeding the plurality of first MRI images to a prediction model, the prediction model having been trained on the basis of reference MRI images by means of supervised learning to predict, from first reference MRI images, at least some of which show an examination region during a first time span after administering a contrast agent, one or more second reference MRI images showing the examination region during a second time span, the second time span following the first time span chronologically,
  generating one or more predicted MRI images showing the examination region during a second time span by means of the prediction model, the second time span following the first time span chronologically,
  displaying and/or outputting the one or more predicted MRI images and/or storing the one or more predicted MRI images in a data storage medium.

The present disclosure further provides for the use of a contrast agent in an MRI method, the MRI method comprising the following steps:
  administering the contrast agent, the contrast agent spreading in an examination region,
  generating a plurality of first MRI images of the examination region during a first time span,
  feeding the generated first MRI images to a prediction model, the prediction model having been trained on the basis of reference MRI images by means of supervised learning to predict, from first reference MRI images showing an examination region during a first time span, one or more second reference MRI images showing the examination region during a second time span, the second time span following the first time span chronologically,
  receiving one or more predicted MRI images showing the examination region during a second time span, as output from the prediction model, the second time span following the first time span chronologically,
  displaying and/or outputting the one or more predicted MRI images and/or storing the one or more predicted MRI images in a data storage medium.

Further provided is a contrast agent for use in an MRI method, the MRI method comprising the following steps:
  administering the contrast agent, the contrast agent spreading in an examination region,
  generating a plurality of first MRI images of the examination region during a first time span,
  feeding the generated first MRI images to a prediction model, the prediction model having been trained on the basis of reference MRI images by means of supervised learning to predict, from first reference MRI images showing an examination region during a first time span, one or more second reference MRI images showing the examination region during a second time span, the second time span following the first time span chronologically, receiving one or more predicted MRI images showing the examination region during a second time span, as output from the prediction model, the second time span following the first time span chronologically, displaying and/or outputting the one or more predicted MRI images and/or storing the one or more predicted MRI images in a data storage medium.

Further provided is a kit comprising a contrast agent and a computer program product according to the disclosure.

The disclosure will be more particularly elucidated below without distinguishing between the subjects of the disclosure (method, system, computer program product, use, contrast agent for use, kit). On the contrary, the following elucidations are intended to apply analogously to all the subjects of the disclosure, irrespective of in which context (method, system, computer program product, use, contrast agent for use, kit) they occur.

If steps are stated in an order in the present description or in the claims, this does not necessarily mean that the disclosure is restricted to the stated order. On the contrary, it is conceivable that the steps are also executed in a different order or else in parallel to one another, unless one step builds upon another step, this absolutely requiring that the building step be executed subsequently (this being, however, clear in the individual case). The stated orders are thus preferred embodiments of the disclosure.

The present disclosure shortens the time span of the examination of an examination object in the generation of MRI images. This is achieved by MRI images of an examination region of the examination object being measured in a first time span (magnetic resonance measurement), and the measured MRI images then being used to predict, with the aid of a self-learning algorithm, one or more MRI images showing the examination region in a second time span. The actual magnetic resonance measurement on the examination object is thus restricted to the first time span and does not encompass the second time span. The MRI images showing the examination region during the first time span contain information allowing a prediction for the second time span.

The "examination object" is usually a living being, preferably a mammal, very particularly preferably a human. The examination region is a portion of the examination object, for example an organ or a portion of an organ. Preferably, the examination region is the liver or a portion of the liver of a mammal (preferably a human).

The "examination region", also called image volume (field of view, FOV), is in particular a volume which is imaged in the magnetic resonance images. The examination region is typically defined by a radiologist, for example on an overview image (localizer). It is self-evident that the examination region can, alternatively or additionally, also be defined automatically, for example on the basis of a selected protocol.

The examination region is introduced into a basic magnetic field. The examination region is subjected to an MRI method and this generates a plurality of MRI images showing the examination region during a first time span. These MRI images generated by measurement during the first time span are also referred to in this description as first MRI images.

The term plurality means that at least two (first) MRI images, preferably at least three (first), very particularly preferably at least four (first) MRI images are generated.

A contrast agent which spreads in the examination region is administered to the examination object. The contrast agent is preferably administered intravenously as a bolus, in a weight-adapted manner (for example, into a vein in the arm).

A "contrast agent" is understood to mean a substance or substance mixture, the presence of which in a magnetic resonance measurement leads to an altered signal. Preferably, the contrast agent leads to a shortening of the T1 relaxation time and/or of the T2 relaxation time.

Preferably, the contrast agent is a hepatobiliary contrast agent such as, for example, Gd-EOB-DTPA or Gd-BOPTA.

In a particularly preferred embodiment, the contrast agent is a substance or a substance mixture with gadoxetic acid or a gadoxetic acid salt as contrast-enhancing active substance. Very particular preference is given to the disodium salt of gadoxetic acid (Gd-EOB-DTPA disodium).

Preferably, the first time span starts before the administration of the contrast agent or with the administration of the contrast agent. It is advantageous when one or more MRI images showing the examination region without contrast agent (native images) are generated, since a radiologist can already gain important information about the state of health of the examination object in such images. For example, a radiologist can identify bleedings in such native MRI images.

The first time span preferably encompasses the contrast agent distributing in the examination region. Preferably, the first time span encompasses the arterial phase and/or the portal-vein phase and/or the late phase in the dynamic contrast-enhancing magnetic resonance tomography of a liver or a portion of a liver of an examination object. The stated phases are, for example, defined and described in the following publications: J. Magn. Reson. Imaging, 2012, 35(3): 492-511, doi:10.1002/jmri.22833; Clujul Medical, 2015, Vol. 88 no. 4: 438-448, DOI: 10.15386/cjmed-414; Journal of Hepatology, 2019, Vol. 71: 534-542, (http://dx.doi.org/10.1016/j.jhep.2019.05.005).

In a preferred embodiment, the first time span is chosen such that such MRI images of the liver or a portion of the liver of an examination object are generated:
  (i) showing the examination region without contrast agent,
  (ii) showing the examination region during the arterial phase, in which the contrast agent spreads in the examination region via the arteries,
  (iii) showing the examination region during the portal-vein phase, in which the contrast agent reaches the examination region via the portal vein, and
  (iv) showing the examination region during the late phase, in which the concentration of the contrast agent in the arteries and veins declines and the concentration of the contrast agent in the liver cells rises.

Preferably, the first time span starts within a time span of from one minute to one second before the administration of the contrast agent, or with the administration of the contrast agent, and lasts for a time span of from 2 minutes to 15 minutes, preferably 2 minutes to 13 minutes, yet more preferably 3 minutes to 10 minutes, from the administration of the contrast agent. Since the contrast agent is renally and biliary excreted very slowly, the second time span can extend up to two hours or more after the administration of the contrast agent.

Figure 1:
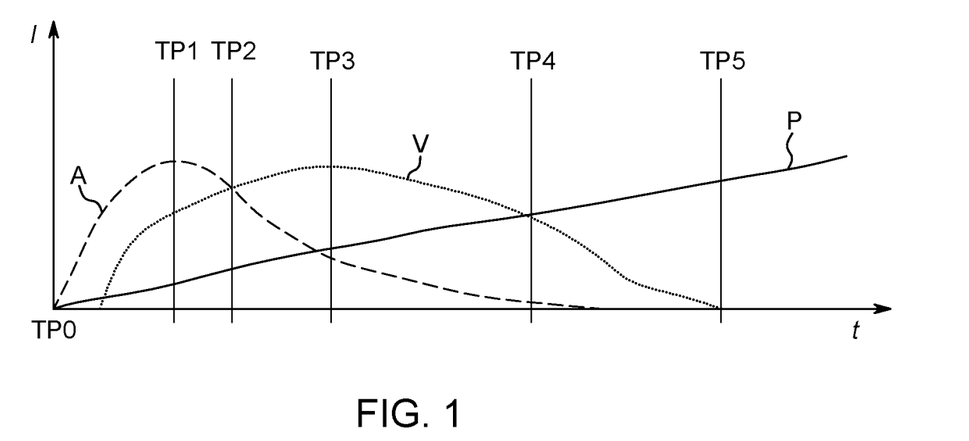
FIG. 1 shows schematically the temporal profile of the concentrations of contrast agent in the liver arteries (A), the liver veins (V) and the liver cells (P) and has already been described in detail above.
Figure 2:
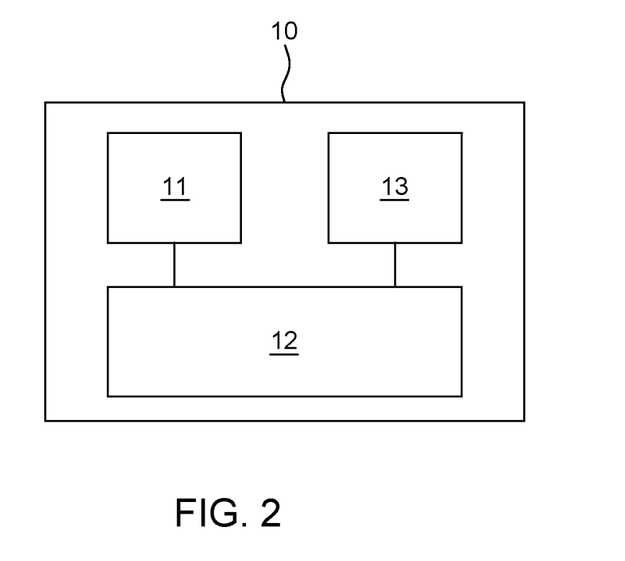
FIG. 2 shows schematically a preferred embodiment of the system according to the disclosure. The system (10) comprises a receiving unit (11), a control and calculation unit (12) and an output unit (13).

Since contrast agent can spread with varying rapidity in different examination objects, the first time span can also be defined via the concentrations of the contrast agent in the different areas of the examination region. One possibility is depicted in FIG. 1. FIG. 1 shows schematically the temporal profile of the concentrations of contrast agent in the liver arteries (A), the liver veins (V) and the healthy liver cells (P). The concentrations are depicted in the form of the signal intensities I in the stated areas (liver arteries, liver veins, liver cells) in the magnetic resonance measurement as a function of the time t. Upon an intravenous bolus injection, the concentration of the contrast agent rises in the liver arteries (A) first of all (dashed curve). The concentration passes through a maximum and then drops. The concentration in the liver veins (V) rises more slowly than in the liver arteries and reaches its maximum later (dotted curve). The concentration of the contrast agent in the healthy liver cells (P) rises slowly (continuous curve) and reaches its maximum only at a very much later time point (the maximum is not depicted in FIG. 1). A few characteristic time points can be defined: At time point TP0, contrast agent is administered intravenously as a bolus. At time point TP1, the concentration (the signal intensity) of the contrast agent in the liver arteries reaches its maximum. At time point TP2, the curves of the signal intensities for the liver arteries and the liver veins intersect. At time point TP3, the concentration (the signal intensity) of the contrast agent in the liver veins passes through its maximum. At time point TP4, the curves of the signal intensities for the liver arteries and the liver cells intersect. At time point T5, the concentrations in the liver arteries and the liver veins have dropped to a level at which they no longer cause a measurable contrast enhancement.

Ina preferred embodiment, the first time span encompasses at least the time points TP0, TP1, TP2, TP3 and TP4.

In a preferred embodiment, at least MRI images of all the following phases are generated (by measurement): in a time span prior to TP0, in the time span from TP0 to TP1, in the time span from TP1 to TP2, in the time span from TP2 to TP3 and in the time span TP3 to TP4.

It is conceivable that, in the time spans prior to TP0, from TP0 to TP1, from TP1 to TP2, from TP2 to TP3 and from TP3 to TP4, one or more MRI images are generated (by measurement) in each case. It is also conceivable that, during one or more time spans, sequences of MRI images are generated (by measurement).

The term sequence means a chronological order, i.e. what are generated are multiple MRI images showing the examination region at successive time points.

A time point is assigned to each MRI image or a time point can be assigned to each MRI image. Usually, this time point is the time point at which the MRI image has been generated (absolute time). A person skilled in the art is aware that the generation of an MRI image uses a certain time span. What can be assigned to an MRI image is, for example, the time point of the start of acquisition or the time point of the completion of acquisition. However, it is also conceivable that arbitrary time points are assigned to the MRI images (e.g. relative time points).

On the basis of a time point, an MRI image can be arranged chronologically with respect to another MRI image; on the basis of the time point of an MRI image, it is possible to establish whether the moment shown in the MRI image took place chronologically before or chronologically after a moment shown in another MRI image.

Preferably, the MRI images are chronologically ordered in a sequence and a plurality such that MRI images showing an earlier state of the examination region are arranged in the sequence and the plurality before those MRI images showing a later state of the examination region.

The time span between two MRI images immediately following one another in a sequence and/or plurality is preferably identical for all pairs of MRI images immediately following one another in the sequence and/or plurality, i.e. the MRI images were preferably generated with a constant acquisition rate.

On the basis of the (first) MRI images generated (by measurement) during the first time span, one second MRI image is predicted or multiple second MRI images are predicted which show the examination region during a second time span. MRI images which are predicted for the second time span are also referred to in this description as second MRI images.

In a preferred embodiment of the present disclosure, the second time span follows the first time span.

The second time span is preferably a time span within the hepatobiliary phase; preferably a time span which starts at least 10 minutes after administration of the contrast agent, preferably at least 20 minutes after administration of the contrast agent.

The plurality of measured MRI images showing the examination region during the first time span is fed to a prediction model. The prediction model is a model configured to predict, on the basis of a plurality of MRI images showing an examination region during a first time span, one or more MRI images showing the examination region during a second time span.

In this connection, the term "prediction" means that the MRI images showing the examination region during the second time span are calculated using the MRI images showing the examination region during the first time span.

The prediction model was preferably created with the aid of a self-learning algorithm in a supervised machine learning process. Learning is achieved by using training data comprising a multiplicity of MRI images of the first and the second time span. These training data are also referred to in this description as reference MRI images. Reference MRI images which have been generated during the first time span are also referred to as first reference MRI images; reference MRI images which have been generated during the second time span are also referred to as second reference MRI images.

The self-learning algorithm generates, during machine learning, a statistical model which is based on the training data. This means that the examples are not simply learnt by heart, but that the algorithm "recognizes" patterns and regularities in the training data. The prediction model can thus also assess unknown data. Validation data can be used to test the quality of the assessment of unknown data.

The prediction model is trained by means of supervised learning, i.e. pluralities of first reference MRI images from the first time span are presented successively to the algorithm and it is "informed" of which second reference MRI images in the second time span are associated with these pluralities. The algorithm then learns a relationship between the pluralities of reference MRI images of the first time span and the reference MRI images of the second time span in order to predict one or more MRI images in the second time span for unknown pluralities of MRI images of the first time span.

Self-learning systems trained by means of supervised learning are widely described in the prior art (see, for example, C. Perez: *Machine Learning Techniques: Supervised Learning and Classification*, Amazon Digital Services LLC—Kdp Print Us, 2019, ISBN 1096996545, 9781096996545).

Preferably, the prediction model is an artificial neural network.

Such an artificial neural network comprises at least three layers of processing elements: a first layer with input neurons (nodes), an N-th layer with at least one output neuron (nodes) and N-2 inner layers, where N is a natural number and greater than 2.

The input neurons serve to receive digital MRI images as input values. Normally, there is one input neuron for each pixel or voxel of a digital MRI image. There can be additional input neurons for additional input values (e.g. information about the examination region, about the examination object, about conditions which prevailed when generating the MRI images and/or information about the time points or time spans at/in which the MRI images were generated).

In such a network, the output neurons serve to predict one or more MRI images of a second time span for a plurality of MRI images of a first time span.

The processing elements of the layers between the input neurons and the output neurons are connected to one another in a predetermined pattern with predetermined connection weights.

Preferably, the artificial neural network is a so-called convolutional neural network (CNN for short).

A convolutional neural network is capable of processing input data in the form of a matrix. This makes it possible to use digital MRI images depicted as a matrix (e.g. width× height×colour channels) as input data. By contrast, a normal neural network, for example in the form of a multilayer perceptron (MLP), requires a vector as input, i.e. to use an MRI image as input, the pixels or voxels of the MRI image would have to be rolled out successively in a long chain. As a result, normal neural networks are, for example, not capable of recognizing objects in an MRI image independently of the position of the object in the MRI image. The same object at a different position in the MRI image would have a completely different input vector.

A CNN consists essentially of filters (convolutional layer) and aggregation layers (pooling layer) which are repeated alternately and, at the end, of one layer or multiple layers of "normal" completely connected neurons (dense/fully connected layer).

When analysing sequences (sequences of MRI image), space and time can be treated as equivalent dimensions and, for example, processed via 3D folds. This has been shown in the papers by Baccouche et al. (see, for example, Baccouche et al.: *Sequential Deep Learning for Human Action Recognition; International Workshop on Human Behavior Understanding, Springer* 2011, pages 29-39) and Ji et al. (3*D Convolutional Neural Networks for Human Action Recognition*, IEEE Transactions on Pattern Analysis and Machine Intelligence, 35(1), 221-231).

Furthermore, it is possible to train different networks which are responsible for time and space and to lastly merge the features, as described in publications by Karpathy et al. and Simonyan & Zisserman (see, for example, Karpathy et al.: *Large-scale Video Classification with Convolutional Neural Networks*; Proceedings of the IEEE conference on Computer Vision and Pattern Recognition, 2014, pages 1725-1732; and Simonyan & Zisserman: *Two-stream Convolutional Networks for Action Recognition in Videos*; Advances in Neural Information Processing Systems, 2014, pages 568-576).

Recurrent Neural Networks (RNNs) are a family of neural networks which contain feedback connections between layers. RNNs allow the modelling of sequential data by common utilization of parameter data via different parts of the neural network. The architecture for an RNN contains cycles. The cycles represent the influence of a current value of a variable on its own value at a future time point, since at least a portion of the output data from the RNN is used as feedback for processing subsequent inputs in a sequence.

Details can be gathered from the prior art (see, for example: S. Khan et al.: *A Guide to Convolutional Neural Networks for Computer Vision*, Morgan & Claypool Publishers 2018, ISBN 1681730227, 9781681730226, WO2018/183044A1, WO2018/200493, WO2019/074938A1, WO2019/204406A1, WO2019/241659A1).

The training of the neural network can, for example, be carried out by means of a backpropagation method. In this connection, what is striven for, for the network, is a mapping of given input data onto given output data that is as reliable as possible. The mapping quality is described by an error function. The goal is to minimize the error function. In the case of the backpropagation method, an artificial neural network is taught by altering the connection weights.

In the trained state, the connection weights between the processing elements contain information regarding the relationship between the pluralities of reference MRI images of the first time span and the reference MRI images of the second time span that can be used in order to predict one or more MRI images showing an examination region during the second time span for new pluralities of MRI images showing the examination region during the first time span.

A cross-validation method can be used in order to divide the data into training and validation data sets. The training data set is used in the backpropagation training of network weights. The validation data set is used in order to check the accuracy of prediction with which the trained network can be applied to unknown pluralities of MRI images.

As already described, further information about the examination object, about the examination region, about examination conditions and/or about the measured MRI images can also be used for training, validation and prediction.

Examples of information about the examination object are: sex, age, weight, height, anamnesis, nature and duration and amount of medicaments already ingested, blood pressure, central venous pressure, breathing rate, serum albumin, total bilirubin, blood sugar, iron content, breathing capacity and the like. These can, for example, also be gathered from a database or an electronic patient file.

Examples of information about the examination region are: pre-existing conditions, operations, partial resection, liver transplantation, iron liver, fatty liver and the like.

It is conceivable that the plurality of MRI images showing the examination region during the first time span are subjected to a movement correction before they are fed to the prediction model. Such a movement correction ensures that a pixel or voxel of a first MRI image shows the same examination region as the corresponding pixel or voxel of a second, temporally downstream MRI image. Movement correction methods are described in the prior art (see, for example: EP3118644, EP3322997, US20080317315, US20170269182, US20140062481, EP2626718).

The present disclosure provides a system which makes it possible to execute the method according to the disclosure.

The system comprises a receiving unit, a control and calculation unit and an output unit.

It is conceivable that the stated units are components of a single computer system; however, it is also conceivable that the stated units are components of multiple separate computer systems which are connected to one another via a network in order to transmit data and/or control signals from one unit to another unit.

A "computer system" is a system for electronic data processing that processes data by means of programmable calculation rules. Such a system usually comprises a "computer", that unit which comprises a processor for carrying out logical operations, and also peripherals.

In computer technology, "peripherals" refer to all devices which are connected to the computer and serve for the control of the computer and/or as input and output devices. Examples thereof are monitor (screen), printer, scanner, mouse, keyboard, drives, camera, microphone, loudspeaker, etc. Internal ports and expansion cards are, too, considered to be peripherals in computer technology.

Computer systems of today are frequently divided into desktop PCs, portable PCs, laptops, notebooks, netbooks and tablet PCs and so-called handhelds (e.g. smartphone); all these systems can be utilized for carrying out the disclosure.

Inputs into the computer system are achieved via input means such as, for example, a keyboard, a mouse, a microphone and/or the like.

The system according to the disclosure is configured to receive pluralities of MRI images showing an examination region during a first time span and to generate (to predict, to calculate), on the basis of these data and optionally further data, one or more MRI images showing the examination region during a second time span.

The control and calculation unit serves for the control of the receiving unit, the coordination of the data and signal flows between various units, and the calculation of MRI images. It is conceivable that multiple control and calculation units are present.

The receiving unit serves for the receiving of pluralities of MRI images. The pluralities can, for example, be transmitted from a magnetic resonance system or be read from a data storage medium. The magnetic resonance system can be a component of the system according to the disclosure. However, it is also conceivable that the system according to the disclosure is a component of a magnetic resonance system.

The sequences of MRI images and optionally further data are transmitted from the receiving unit to the control and calculation unit.

The control and calculation unit is configured to predict, on the basis of the pluralities of MRI images showing an examination region during a first time span, one or more MRI images, the predicted MRI images showing the examination region during a second time span. Preferably, what can be loaded into a memory of the control and calculation unit is a prediction model which is used to calculate the MRI images of the second time span. The prediction model was preferably generated (trained) with the aid of a self-learning algorithm by means of supervised learning.

Via the output unit, the predicted MRI images can be displayed (e.g. on a screen), be outputted (e.g. via a printer) or be stored in a data storage medium.

The disclosure is more particularly elucidated below with reference to figures, without wishing to restrict the disclosure to the features or combinations of features that are shown in the figures, where.

Figure 3:
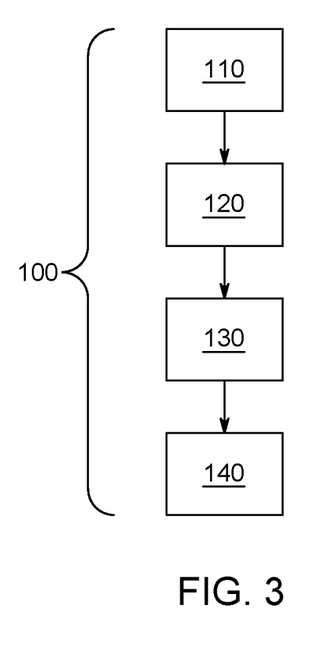
FIG. 3 shows schematically and exemplarily one embodiment of the method according to the disclosure. The method (100) comprises the steps.

(110) receiving a plurality of first MRI images, at least some of the first MRI images showing an examination region during a first time span after administering a contrast agent, (120) feeding the plurality of first MRI images to a prediction model, the prediction model having been trained on the basis of reference MRI images by means of supervised learning to predict, from first reference MRI images showing an examination region during a first time span, one or more second reference MRI images showing the examination region during a second time span, the second time span following the first time span chronologically, (130) generating one or more predicted MRI images showing the examination region during a second time span by means of the prediction model, the second time span following the first time span chronologically, (140) displaying and/or outputting the one or more predicted MRI images and/or storing the one or more predicted MRI images in a data storage medium.

Figure 4:
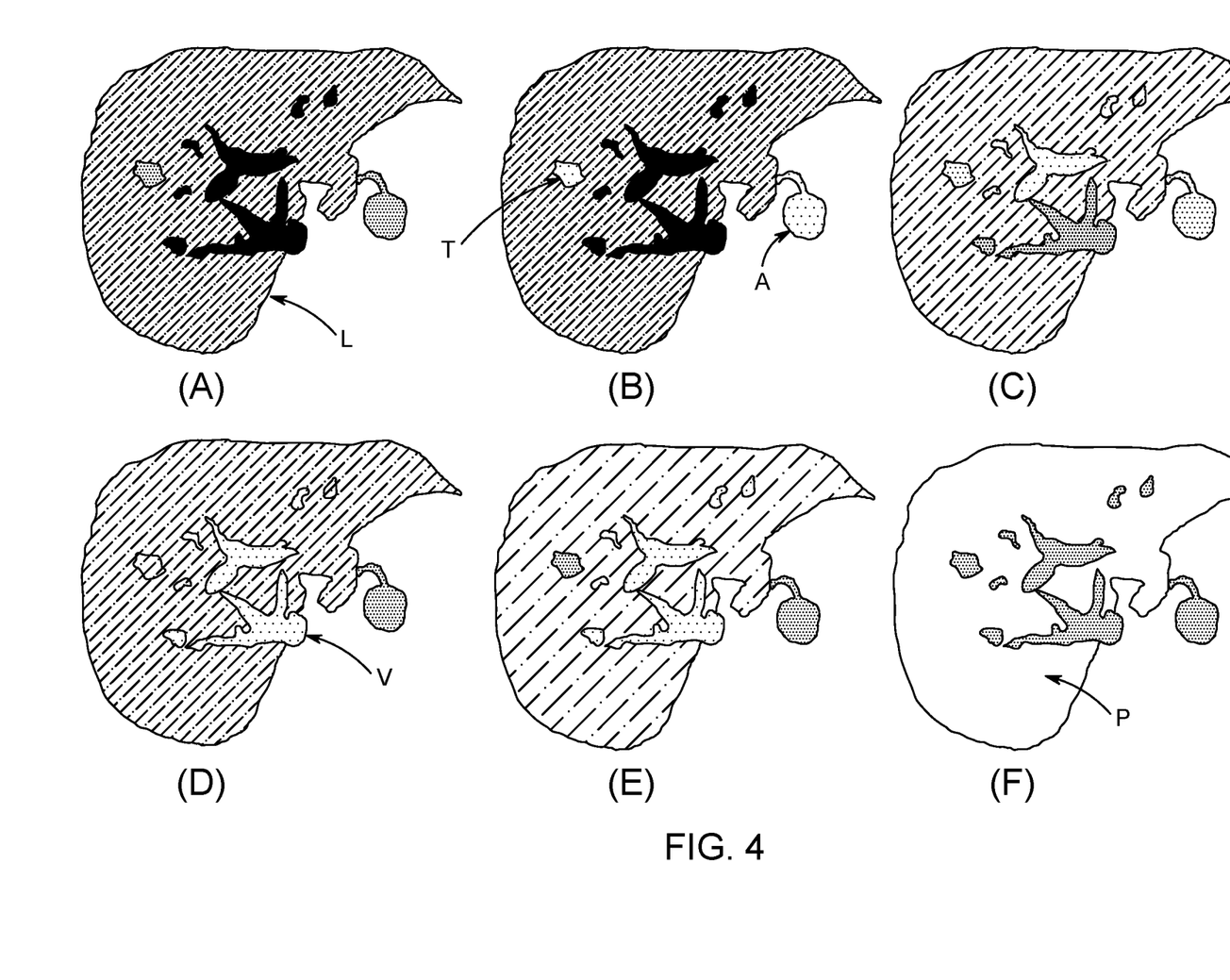

FIG. 4 shows schematically and exemplarily a plurality of MRI images of the liver during the dynamic and the hepatobiliary phase. In FIGS. 4(a), 4(b), 4(c), 4(d), 4(e) and 4(f), the same cross section through the liver at different time points is always depicted. The reference signs entered in FIGS. 4(a), 4(b), 4(d) and 4(f) apply to all of FIGS. 4(a), 4(b), 4(c), 4(d), 4(e) and 4(f); they are each entered only once merely for the sake of clarity.

FIG. 4(a) shows the cross section through the liver (L) before the intravenous administration of a hepatobiliary contrast agent. At a time point between the time points depicted by FIGS. 4(a) and 4(b), a hepatobiliary contrast agent was administered intravenously as a bolus. This reaches the liver via the liver artery (A) in FIG. 4(b). Accordingly, the liver artery is depicted with signal enhancement (arterial phase). A tumour (T), which is supplied with blood mainly via arteries, likewise stands out from the liver-cell tissue as a lighter (signal-enhanced) region. At the time point depicted in FIG. 4(c), the contrast agent reaches the liver via the veins. In FIG. 4(d), the venous blood vessels (V) stand out from the liver tissue as light (signal-enhanced) regions (venous phase). At the same time, the signal intensity in the healthy liver cells, which are supplied with contrast agent mainly via the veins, continuously rises (FIG. 4(c)→4(d)→4(e)→4(f)). In the hepatobiliary phase depicted in FIG. 4(f), the liver cells (P) are depicted with signal enhancement; the blood vessels and the tumour no longer have contrast agent and are accordingly depicted darkly.

Figure 5:
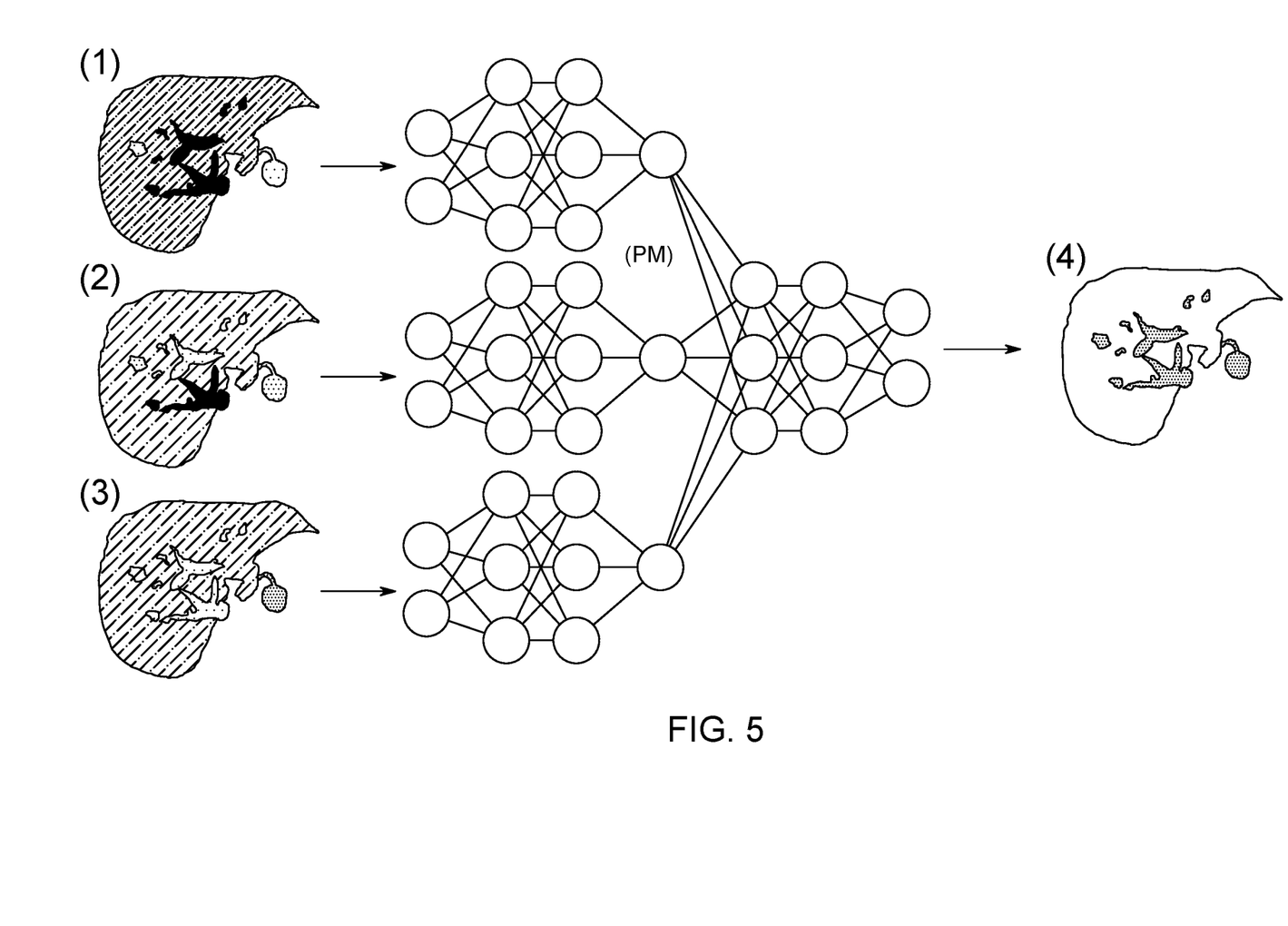

FIG. 5 shows exemplarily and schematically how three MRI images (1), (2) and (3) showing a liver in a first time span are fed to a prediction model (PM). The prediction model calculates from the three MRI images (1), (2) and (3) an MRI image (4) showing the liver in a second time span. The MRI images (1), (2) and (3) can, for example, show the MRI images shown in FIGS. 4(b), 4(c) and 4(d), The MRI image (4) can, for example, be the MRI image shown in FIG. 4(f).

The invention claimed is:

1. A computer-implemented method comprising:
receiving a plurality of magnetic resonance imaging (MRI) images, wherein at least one received MRI image of the plurality of MRI images shows an examination region before administering a contrast agent, and at least one received MRI image of the plurality of MRI images shows the examination region during a first time span after administering the contrast agent;

feeding the plurality of MRI images to a prediction model, the prediction model having been trained by means of supervised learning to predict based on MRI images, at least some of which show the examination region during the first time span after administering the contrast agent, one or more MRI images showing the examination region during a second time span, the second time span following the first time span chronologically;

generating one or more predicted MRI images showing the examination region during the second time span by means of the prediction model, the second time span following the first time span chronologically; and displaying and/or outputting the one or more predicted MRI images and/or storing the one or more predicted MRI images in a data storage medium.

2. The method of claim 1, wherein the examination region is a liver or a portion of a liver of a mammal.

3. The method of claim 2, wherein the first time span is chosen such that it shows the examination region in different phases, wherein the phases comprise a native phase, an arterial phase, a portal-vein phase, and a late phase, wherein at least one MRI image is received which shows the examination region in the native phase, at least one MRI image is received which shows the examination region during the arterial phase, at least one MRI image is received which shows the examination region in the portal-vein phase, and at least one MRI image is received which shows the examination region in the late phase.

4. The method of claim 1, wherein the plurality of MRI images show a liver or a portion of a liver of a mammal prior to a time point TP0 and during a time span from TP0 to TP1 and/or during a time span from TP1 to TP2 and/or during a time span from TP2 to TP3 and/or during a time span from TP3 to TP4, at time point TP0 the contrast agent being administered intravenously as a bolus and then reaching liver cells via liver arteries and liver veins, at time point TP1 the contrast agent in the liver arteries reaching a maximum concentration, at time point TP2 a signal intensity generated in the liver veins by the contrast agent assuming a value which is the same size as a value of a signal intensity generated in the liver arteries by the contrast agent, at time point TP3 the contrast agent in the liver veins reaching a maximum concentration, at time point TP4 a signal intensity generated in the liver cells by the contrast agent assuming a value which is the same size as a value of a signal intensity generated in the liver veins by the contrast agent.

5. The method of claim 1, wherein the first time span starts within a time span of from one minute to one second before administration of the contrast agent or with the administration of the contrast agent, and lasts for a time span of from 2 minutes to 15 minutes from the administration of the contrast agent.

6. The method of claim 1, wherein the second time span is within a hepatobiliary phase.

7. The method of claim 1, wherein the second time span starts at least 10 minutes after administration of the contrast agent.

8. The method of claim 1, wherein the prediction model is an artificial neural network.

9. The method of claim 1, wherein the contrast agent is a hepatobiliary contrast agent.

10. A system comprising:
a receiving unit;
a control and calculation unit; and
an output unit; wherein the control and calculation unit being configured to prompt the receiving unit to receive a plurality of magnetic resonance imaging (MRI) images, wherein at least one received MRI image of the plurality of MRI images shows an examination region before administering a contrast agent, and at least one received MRI image of the plurality of MRI images shows the examination region during a first time span after administering the contrast agent, the control and calculation unit being configured to predict one or more MRI images based on the plurality of MRI images, the one or more predicted MRI images showing the examination region during a second time span, the second time span following the first time span chronologically, and the control and calculation unit being configured to prompt the output unit to display the one or more predicted MRI images, to output the one or more predicted MRI images, or to store the one or more predicted MRI images in a data storage medium.

11. A computer program product comprising at least one non-transitory computer-readable medium comprising one or more instructions that, when executed by a computer system, cause the computer system to execute the following:
receiving a plurality of magnetic resonance imaging (MRI) images, wherein at least one received MRI image of the plurality of MRI images shows an examination region before administering a contrast agent, and at least one received MRI image of the plurality of MRI images shows the examination region during a first time span after administering the contrast agent;

feeding the plurality of MRI images to a prediction model, the prediction model having been trained by means of supervised learning to predict based on MRI images, at least some of which show the examination region during the first time span after administering the contrast agent, one or more MRI images showing the examination region during a second time span, the second time span following the first time span chronologically;

generating one or more predicted MRI images showing the examination region during the second time span by means of the prediction model, the second time span following the first time span chronologically; and displaying and/or outputting the one or more predicted MRI images and/or storing the one or more predicted MRI images in a data storage medium.

12. Use of a contrast agent in a magnetic resonance imaging (MRI) method, the MRI method comprising the following:
administering the contrast agent, the contrast agent spreading in an examination region;
generating a plurality of MRI images, the plurality of MRI images comprising at least one MRI image of the examination region before administering the contrast agent and comprising at least one MRI image of the examination region during a first time span after administering the contrast agent;
feeding the generated MRI images to a prediction model, the prediction model having been trained by means of supervised learning to predict, based on MRI images showing the examination region during the first time span, one or more MRI images showing the examination region during a second time span, the second time span following the first time span chronologically;
receiving one or more predicted MRI images showing the examination region during the second time span, as output from the prediction model, the second time span following the first time span chronologically; and displaying and/or outputting the one or more predicted MRI images and/or storing the one or more predicted MRI images in a data storage medium.

13. A kit comprising a contrast agent and the computer program product as claimed in claim 11.

14. The use of the contrast agent in the MRI method of claim 12, wherein the contrast agent is preferably a substance or a substance mixture with gadoxetic acid or a gadoxetic acid salt as contrast-enhancing active substance.

15. The computer program product of claim 11, wherein the first time span is chosen such that it shows the examination region in different phases, wherein the phases comprise a native phase, an arterial phase, a portal-vein phase, and a late phase, wherein at least one MRI image is received which shows the examination region in the native phase, at least one MRI image is received which shows the examination region during the arterial phase, at least one MRI image is received which shows the examination region in the portal-vein phase, and at least one MRI image is received which shows the examination region in the late phase.

16. The computer program product of claim 11, wherein the plurality of MRI images show a liver or a portion of a liver of a mammal prior to a time point TP0 and during a time span from TP0 to TP1 and/or during a time span from TP1 to TP2 and/or during a time span from TP2 to TP3 and/or during a time span from TP3 to TP4, at time point TP0 the contrast agent being administered intravenously as a bolus and then reaching liver cells via liver arteries and liver veins, at time point TP1 the contrast agent in the liver arteries reaching a maximum concentration, at time point TP2 a signal intensity generated in the liver veins by the contrast agent assuming a value which is the same size as a value of a signal intensity generated in the liver arteries by the contrast agent, at time point TP3 the contrast agent in the liver veins reaching a maximum concentration, at time point TP4 a signal intensity generated in the liver cells by the contrast agent assuming a value which is the same size as a value of a signal intensity generated in the liver veins by the contrast agent.

17. The computer program product of claim 11, wherein the first time span starts within a time span of from one minute to one second before administration of the contrast agent or with the administration of the contrast agent, and lasts for a time span of from 2 minutes to 15 minutes.

18. The computer program product of claim 11, wherein the second time span is within a hepatobiliary phase.

19. The computer program product of claim 11, wherein the prediction model is an artificial neural network.

* * * * *